(12) United States Patent
Baehr

(10) Patent No.: US 7,524,105 B2
(45) Date of Patent: Apr. 28, 2009

(54) OPTICAL DILATOMETER

(75) Inventor: Heinz Baehr, Bad Oeynhausen (DE)

(73) Assignee: BAEHR - Thermoanalyse GmbH, Huellhurst (DE)

( * ) Notice: Subject to any disclaimer, the term of this patent is extended or adjusted under 35 U.S.C. 154(b) by 177 days.

(21) Appl. No.: 11/790,268

(22) Filed: Apr. 24, 2007

(65) Prior Publication Data

US 2007/0248140 A1 Oct. 25, 2007

(30) Foreign Application Priority Data

Apr. 24, 2006 (DE) ............ 10 2006 019 433

(51) Int. Cl.
*G01N 25/00* (2006.01)
(52) U.S. Cl. ............... 374/55; 356/634
(58) Field of Classification Search ............ 374/55, 374/187, 195; 356/634
See application file for complete search history.

(56) References Cited

U.S. PATENT DOCUMENTS 4,924,477 A * 5/1990 Gilmore et al. ............ 374/55
5,479,261 A * 12/1995 Hansen ..................... 356/628
6,476,922 B2 * 11/2002 Paganelli ................... 356/634
6,767,127 B2 * 7/2004 Paganelli ................... 374/55
2002/0044288 A1 * 4/2002 Paganelli ................... 356/625
2003/0108082 A1 * 6/2003 Paganelli ................... 374/55

FOREIGN PATENT DOCUMENTS

EP 1 329 687 A2 7/2003

\* cited by examiner

*Primary Examiner*—Andre J Allen
(74) *Attorney, Agent, or Firm*—Crowell & Moring LLP

(57) ABSTRACT

An optical dilatometer includes a furnace, in which a sample may be laid on a sample carrier, and an optical system for measuring a length of the sample at different temperatures, windows for the passage of beams being provided on a sample chamber of the furnace. A light source and a collimator for generating a parallel beam path are situated on one side of the furnace, the length of the sample being detectable via a silhouette image by a sensor, situated on the diametrically opposite side of the furnace from the light source, and a lens system. This allows a simple length measurement without orientation of an optical system.

20 Claims, 6 Drawing Sheets

OPTICAL DILATOMETER

CROSS REFERENCE TO RELATED APPLICATIONS

This application claims priority under 35 U.S.C. § 119 to German Patent Application No. 10 2006 019 433.0-52, filed Apr. 24, 2006, the entire disclosure of which is herein expressly incorporated by reference.

BACKGROUND AND SUMMARY OF THE INVENTION

The present invention relates to an optical dilatometer, including a furnace, in which a sample may be laid on a sample carrier, and an optical system for measuring a length of the sample at different temperatures.

Dilatometers are measuring devices, which measure the linear thermal expansion of a sample as a function of the temperature. An optical dilatometer is known from European Patent Document EP 1 329 687, in which a holder for the sample is situated between two optical systems. The sample is enclosed by a tubular furnace body, so that corresponding temperature changes may act on the sample. For a measurement of the length change, a sample is laid in a furnace and one of the optical systems is pointed at one end of the sample and the other optical system is pointed at the other end of the sample. This orientation of the optical systems and/or the sample is comparatively complex.

The present invention is therefore based on the object of providing a dilatometer which is easy to handle and has a simple construction.

According to an exemplary embodiment of the present invention, a light source and a collimator for generating a parallel beam path are situated on one side of a furnace, and the length of a sample is detectable via a silhouette image by a sensor situated on the diametrically opposite side. The necessity of orienting the optical system or the sample is thus dispensed with, because the sample may be measured at any arbitrary point on the sample carrier.

According to another exemplary embodiment of the present invention, a filter is provided on the receiver side which is only transparent to beams of a specific wavelength, which are emitted on a side of a light source. Interfering influences due to light or beams having another wavelength may thus be precluded relatively reliably.

A telecentric optical system may be situated on the receiver side. The silhouette image of the sample may be imaged on a sensor which may be implemented as a high-speed linear CCD sensor to automatically detect the sample length. For a rapid and simple measurement, the sensor may be connected to an A/D converter, which is connected to a controller for recognizing the boundary of the acquired image.

For especially precise measurement, the light source is formed by a high-power GaN LED, whose light has an especially constant wavelength. A diffuser may also be situated between the light source and the collimator.

To implement a uniform temperature profile, the sample chamber has a cylindrical shape, the sample carrier being situated radially centered in the sample chamber and between a top and bottom heating element. Windows transparent to the beam path are provided on diametrically opposite sides of the sample chamber.

An advantageous construction of the furnace results through a furnace body divided into a top part and a bottom part, the partition plane between the top part and the bottom part passing through the sample chamber between the top and bottom heating elements. As a result, the top part may be removed from the bottom part of the furnace body, because of which the sample chamber is easily accessible. It is also possible to charge the sample changer using robot technology very easily. The furnace body expediently has a cylindrical basic shape, whose axis is coincident with that of the sample chamber. The furnace is designed for operation under vacuum and protective gas. Corresponding precautions such as seal elements at the partition plane and the optical windows guarantee this type of operation.

Other objects, advantages and novel features of the present invention will become apparent from the following detailed description of the invention when considered in conjunction with the accompanying drawings.

DETAILED DESCRIPTION OF THE DRAWINGS

Figure 1:
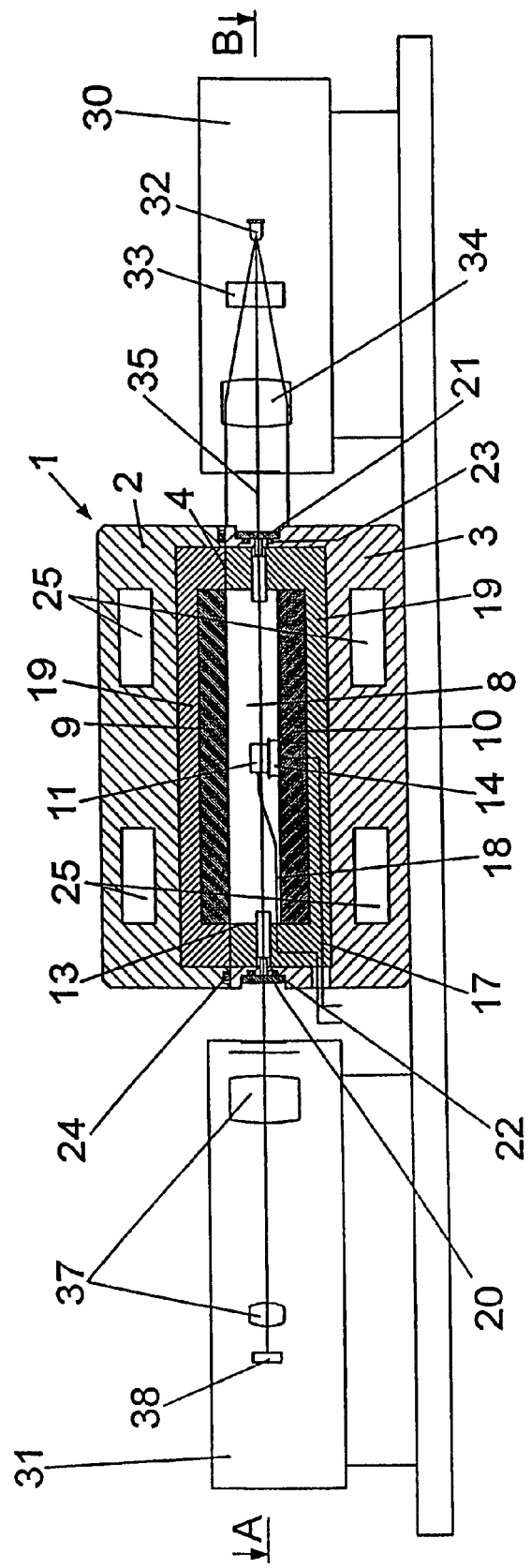
FIG. 1 shows a sectional side view of an exemplary embodiment of a furnace according to the present invention.
Figure 2:
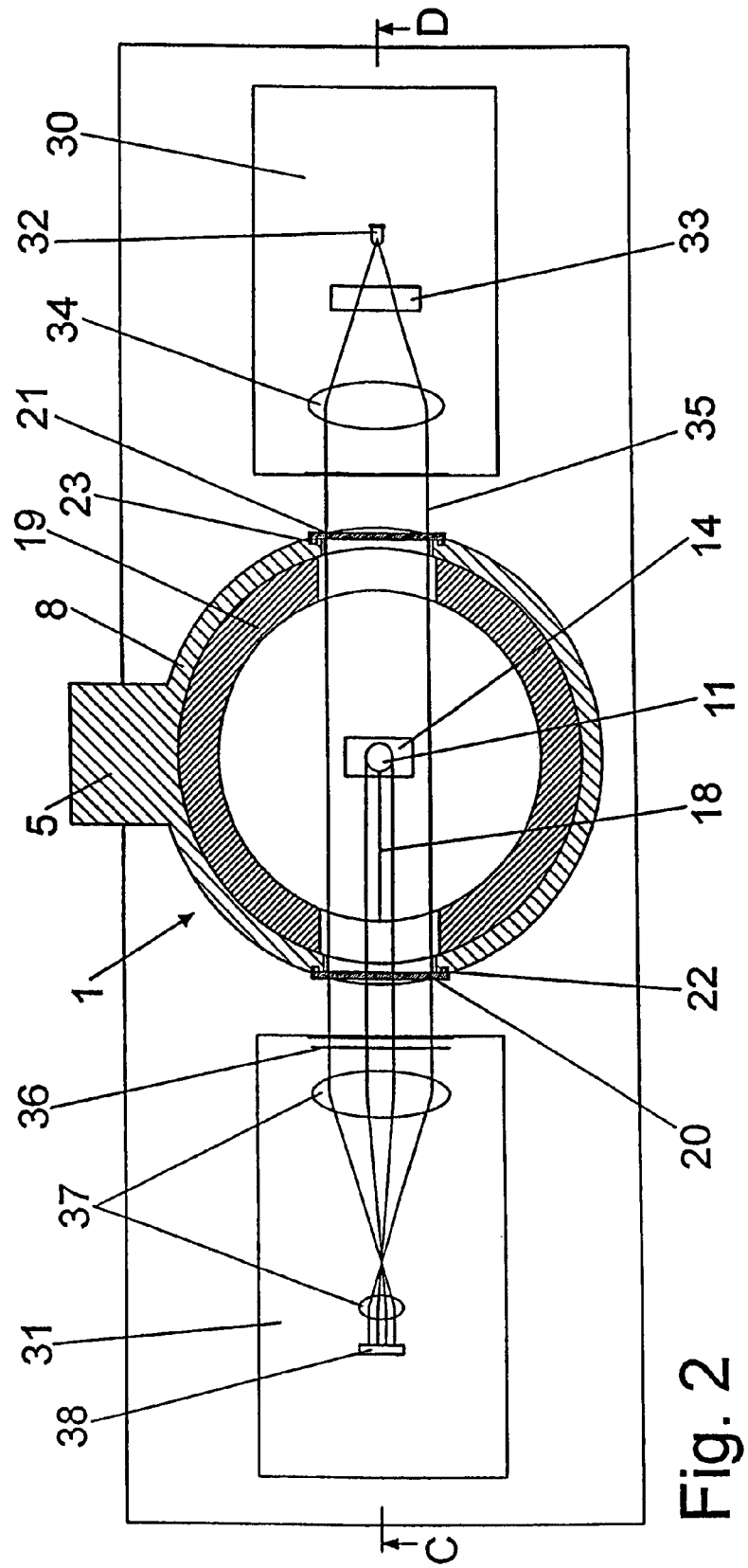
FIG. 2 shows a sectional top view of the furnace of FIG. 1.
Figure 3:
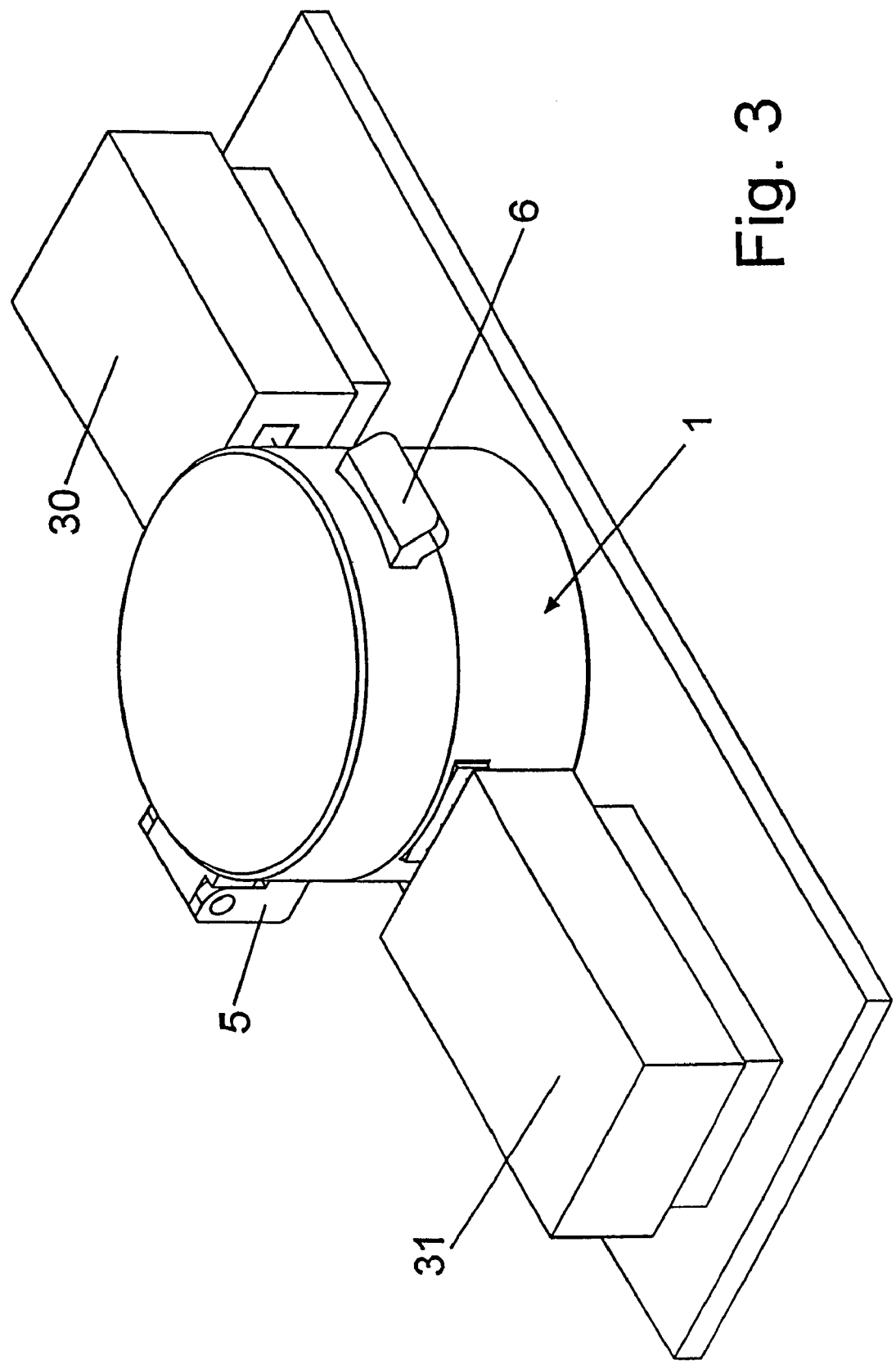
FIG. 3 shows a perspective view of the furnace of FIG. 1.
Figure 4:
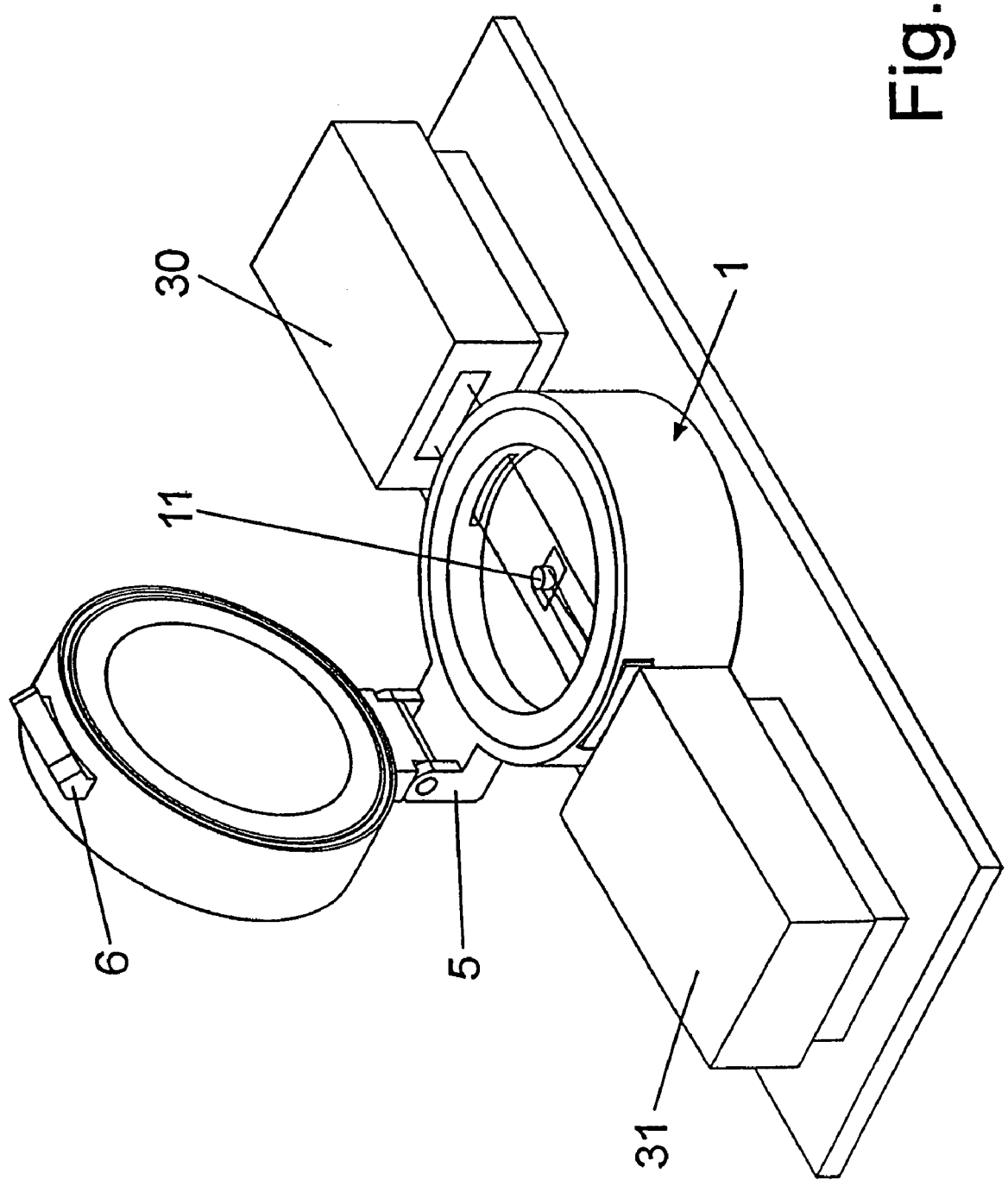
FIG. 4 shows a perspective view of the furnace of FIG. 1 having an open top part.

FIGS. 1 through 4 show a dilatometer having a furnace 1, which has a cylindrical basic shape. The furnace 1 is divided into a top part 2 and a bottom part 3, which may be lifted apart and put one on top of the other congruently along a horizontally running partition plane 4. The top part 2 may be raised and lowered via a hinge 5, which is attached to the top part 2 and the bottom part 3. A handle 6 is provided on the top part 2 on the diametrically opposite side.

The top part 2 and the bottom part 3 centrally enclose a sample chamber 8, which has a flat, hollow-cylindrical design and is situated coaxially in the furnace body 1 in the interior of the cylindrical furnace body 1. The sample chamber 8 is closed by lowering the top part 2 onto the bottom part 3. The sample chamber 8 is delimited on top by a heating element 9, which may essentially have the shape of a circular disk, for example, which is situated on the bottom side of the top part 2 toward the partition plane 4. Analogously, the sample chamber 8 is delimited on the bottom by a bottom heating element 10, the circular heating elements 9 and 10 being congruent with one another.

The hollow-cylindrical sample chamber 8 has a height which is multiple times smaller than the diameter of the sample chamber 8. The sample chamber is enclosed by a lateral wall 13 in the form of a peripheral cylinder mantle inner surface, over which the seam of the partition plane 4 runs. The diameter of the sample chamber 8 is approximately equal to that of the top and bottom heating elements 9 and 10, which are enclosed around their circumference by thermal insulation 19. The thermal insulation in the top part 2 and in the bottom part 3 of the furnace body 1 is situated in such a way that when the top part 2 is closed, the sample chamber 8 is thermally insulated and may be heated to high temperatures of up to 2000° C., for example.

A pedestal 14, which has a flat, horizontal top side, is situated centrally in the sample chamber 8 as a sample carrier. A sample 11, which may be put down from above, lies on the pedestal 14. The sample 11 may be laid on any point of the pedestal 14 in the area of a beam path 35 for a measurement, a uniform temperature profile resulting in the area of the pedestal 14 due to the configuration of the heating elements 9 and 10.

A sample thermocouple 18 is also located in proximity to the pedestal 14, and a regulating thermocouple 17 is located in or on the heating disk 10. Furthermore, a water cooling unit 25 is also provided in the top part 2 and the bottom part 3 for operating the furnace 1 at high temperatures.

An optical system is situated neighboring the furnace 1, which measures the length change of the sample 11 as a function of the temperature.

The optical system includes an optical transmitter 30 and a receiver 31. The transmitter 30 has a light source in the form of a high-power GaN LED 32, which emits light having a very constant wavelength, and a diffusion unit 33, as well as a collimator lens 34, which emits the light in parallel. The parallel beam path 35 thus generated passes through a window 21 implemented in the bottom part 3 and is incident there on the sample 11. The beam path 35 is implemented as somewhat broader than the width of the sample carrier 14. Only beams which are not incident on the sample 11 exit again through a window 20, which is situated on the side of the bottom part 3 diametrically opposite the window 21.

The window 21 is attached via a seal 23 and the window 20 is attached via a seal 22 to a side wall of the sample chamber 8. Furthermore, the top part 2 is situated sealed by a seal 24 on the bottom part 3, so that the sample chamber 8 may be provided with a gas filling or with a vacuum.

Shadow beams result due to the light source 32 and the sample 11, which are first incident on a filter 36 on the receiver side 31. The filter 36 may be implemented in such a way that it only transmits the beams having the wavelength emitted by the high-power GaN LED 32. Subsequently, the beams pass through a telecentric optical system 37 having one or more lenses and are then incident on a high-speed linear CCD sensor 38. The signals of the sensor 38 are relayed for analysis to an A/D converter and then to a digital boundary recognition processor and to the CPU.

Figure 5:
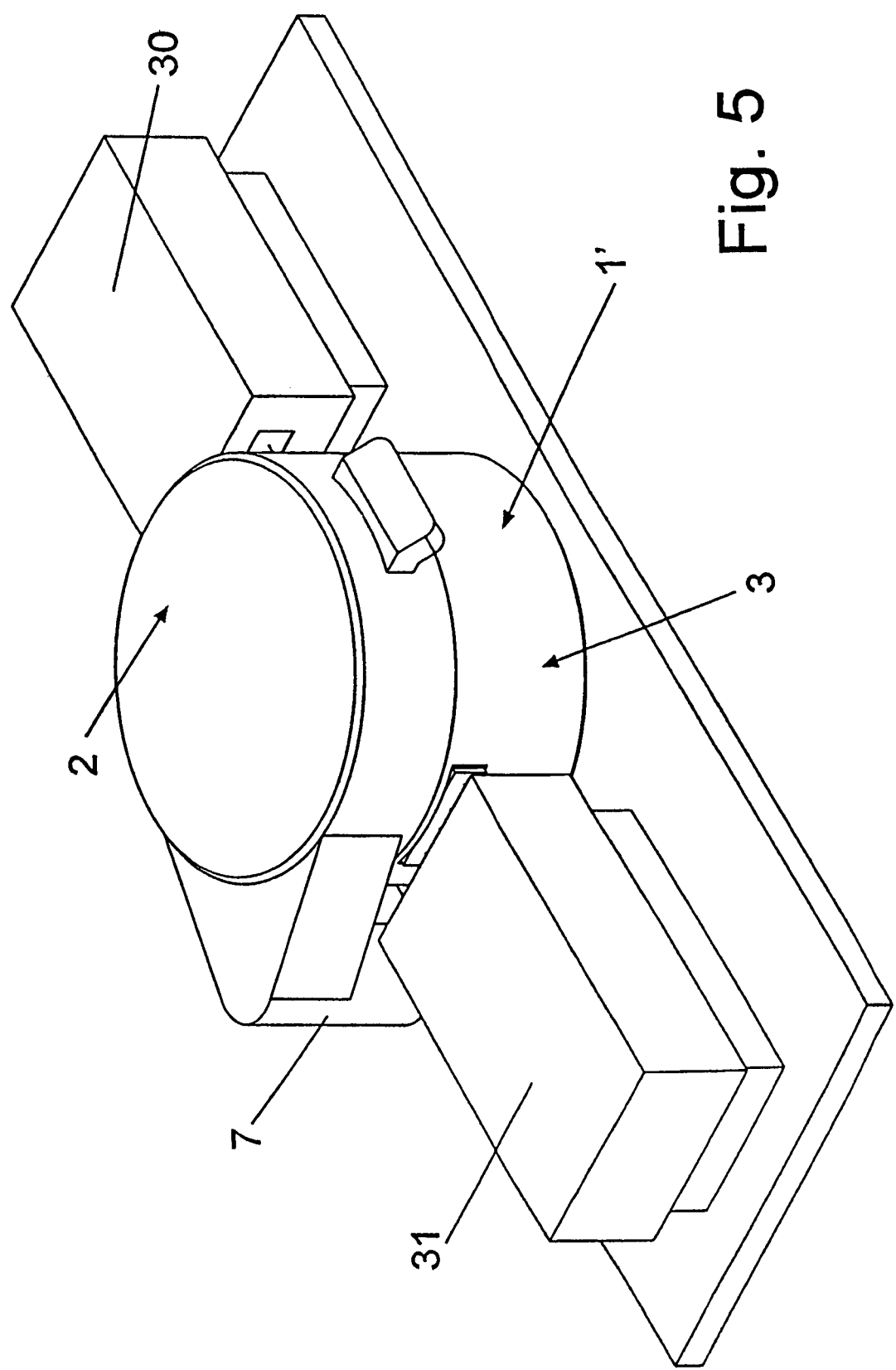
FIG. 5 shows a perspective view of a modified exemplary embodiment.
Figure 6:
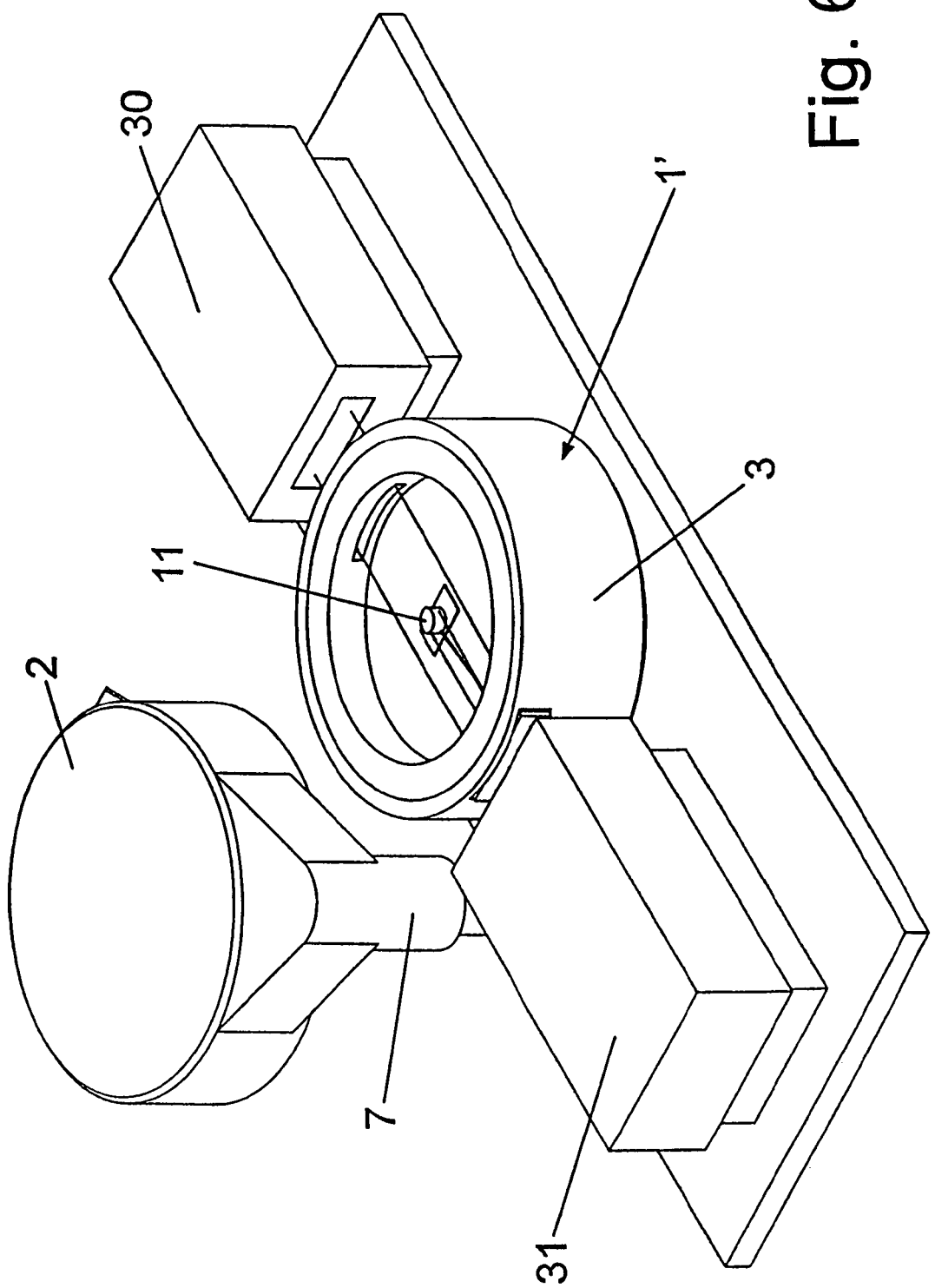
FIG. 6 shows a perspective view of the furnace of FIG. 5 having an open top part.

A modified embodiment of a furnace 1' is shown in FIGS. 5 and 6, in which a lift and pivot mechanism 7 is provided instead of the hinge 5. The top part 2 is raised and pivoted away laterally from the bottom part 3 by the lift and pivot mechanism 7, so that the sample chamber 8 is accessible from above to insert or remove the sample 11. Otherwise, the furnace 1' is implemented as in the preceding exemplary embodiment.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An optical dilatometer, comprising:
 a furnace, including
  a sample carrier on which a sample may be laid,
  a sample chamber, and
  windows provided on the sample chamber for the passage of beams; and
 an optical system for measuring a length of the sample at different temperatures, the optical system including
  a light source and a collimator, situated on one side of the furnace, for generating a parallel beam path, and
  a sensor, situated on the diametrically opposite side of the furnace from the light source, for detecting a length of the sample via a silhouette image.

2. The dilatometer according to claim 1, further comprising a filter provided on a receiver side of the optical system, which is only transparent to beams of a specific wavelength, and to beams which are emitted on a side of the light source.

3. The dilatometer according to claim 1, further comprising a telecentric optical system situated on a receiver side of the optical system.

4. The dilatometer according to claim 1, wherein the sensor is a high-speed linear CCD sensor.

5. The dilatometer according to claim 1, wherein the sensor is connected to an A/D converter, which is connected to a controller for recognizing a boundary of an acquired image.

6. The dilatometer according to claim 1, wherein the light source comprises a high-power GaN LED.

7. The dilatometer according to claim 1, further comprising a diffuser situated between the light source and the collimator.

8. The dilatometer according to claim 1, wherein a width of the beam path is greater than a width of the sample carrier.

9. The dilatometer according to claim 1, wherein the sample chamber has a cylindrical shape, the sample carrier is situated radially centered in the sample chamber, and the windows are transparent to the beam path and are situated on diametrically opposite sides of the sample chamber.

10. The dilatometer according to claim 1, wherein the furnace is divided into a top part and a bottom part, a horizontal partition plane being formed between the top part and the bottom part, and the sample being freely accessible from above when the sample chamber is opened.

11. The dilatometer according to claim 2, further comprising a telecentric optical system situated on a receiver side of the optical system.

12. The dilatometer according to claim 2, wherein the sensor is a high-speed linear CCD sensor.

13. The dilatometer according to claim 2, wherein the sensor is connected to an A/D converter, which is connected to a controller for recognizing a boundary of an acquired image.

14. The dilatometer according to claim 2, wherein the light source comprises a high-power GaN LED.

15. The dilatometer according to claim 2, further comprising a diffuser situated between the light source and the collimator.

16. The dilatometer according to claim 2, wherein a width of the beam path is greater than a width of the sample carrier.

17. The dilatometer according to claim 2, wherein the sample chamber has a cylindrical shape, the sample carrier is situated radially centered in the sample chamber, and the windows are transparent to the beam path and are situated on diametrically opposite sides of the sample chamber.

18. The dilatometer according to claim 2, wherein the furnace is divided into a top part and a bottom part, a horizontal partition plane being formed between the top part and the bottom part, and the sample being freely accessible from above when the sample chamber is opened.

19. The dilatometer according to claim 3, wherein the sensor is a high-speed linear CCD sensor.

20. A method for measuring a length of a sample at a plurality of temperatures in an optical dilatometer that includes a furnace and an optical system, the method comprising:
 generating a parallel beam path with a light source and a collimator of the optical system that are situated on one side of the furnace, the parallel beam path passing through windows on a sample chamber of the furnace;
 irradiating the sample with the parallel beam path; and
 detecting a length of the sample with a sensor situated on a diametrically opposite side of the furnace from the light source via a silhouette image of the sample.

* * * * *